(12) United States Patent
Haubeil

(10) Patent No.: US 6,539,941 B2
(45) Date of Patent: Apr. 1, 2003

(54) FILTERED RESUSCITATION BAG VALVE MASK AND ADAPTER

(76) Inventor: George W. Haubeil, 1465 Canterbury Rd., Front Royal, VA (US) 22630

( * ) Notice: Subject to any disclaimer, the term of this patent is extended or adjusted under 35 U.S.C. 154(b) by 86 days.

(21) Appl. No.: 09/789,709

(22) Filed: Feb. 22, 2001

(65) Prior Publication Data

US 2001/0029950 A1 Oct. 18, 2001

Related U.S. Application Data

(60) Provisional application No. 60/183,776, filed on Feb. 22, 2000.

(51) Int. Cl.[7] ............................. A62B 7/10; A61M 16/00
(52) U.S. Cl. ............................. 128/205.13; 128/205.12; 128/203.11
(58) Field of Search ................ 128/205.13, 205.16, 128/203.11, 205.29, 909, 912, 205.12

(56) References Cited

U.S. PATENT DOCUMENTS

| | | | | | |
|---|---|---|---|---|---|
| 3,556,097 | A | * | 1/1971 | Wallace | 128/202.23 |
| 4,945,918 | A | * | 8/1990 | Abernathy | 128/202.13 |
| 5,154,167 | A | * | 10/1992 | Hepburn | 128/200.24 |
| 5,345,929 | A | * | 9/1994 | Jansson et al. | 128/205.13 |
| 5,357,951 | A | * | 10/1994 | Ratner | 128/205.12 |
| 5,727,542 | A | * | 3/1998 | King | 128/200.18 |
| 5,752,502 | A | * | 5/1998 | King | 128/200.18 |

* cited by examiner

Primary Examiner—Henry Bennett
Assistant Examiner—Alfred Basichas
(74) Attorney, Agent, or Firm—Cahn & Samuels, LLP

(57) ABSTRACT

A portable bag valve mask resuscitator including an air intake adapter for attachment of an air filter cartridge for filtering air administered during manual resuscitation procedures and a method for converting bag mask resuscitators.

9 Claims, 2 Drawing Sheets

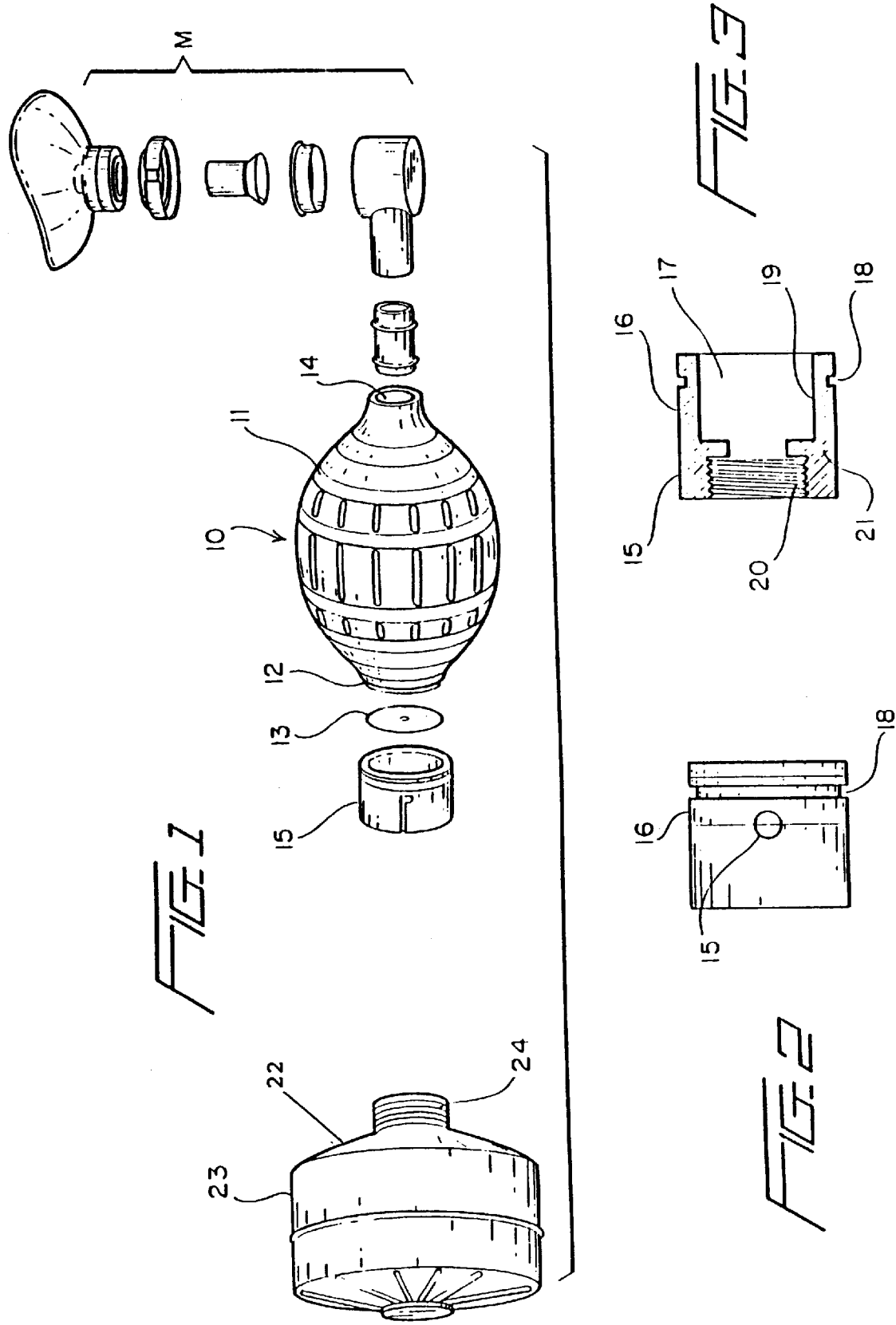

DEMAND VALVE
ASSEMBLIES 26

Figure 4

FILTERED RESUSCITATION BAG VALVE MASK AND ADAPTER

CROSS-REFERENCE TO RELATED APPLICATIONS

This application claims the benefit of U.S. Provisional application Serial No. 60/183,776 filed Feb. 22, 2000.

RIGHTS OF THE GOVERNMENT

The invention described herein may be manufactured and used by or for the Government of the United States for all governmental purposes without the payment of any royalty.

TECHNICAL FIELD

The present invention relates to improvements in bag valve mask resuscitators and, more particularly, a C2 type air filter cartridge attachment adjunct and method for use with manually-operated Bag Valve Masks (BVM) such as Flynn resuscitation bag masks.

BACKGROUND OF THE INVENTION

Resuscitation bag masks are commonly used in emergency care and critical care situations. When used in the field bag masks deliver air under positive pressure to a patient not then capable of breathing independently. In a contaminated environment, forcibly delivered unfiltered air exposes the patient to additional hazards, a undesirable product of the caregiver's efforts. By positively delivering unfiltered air via a bag mask to a patient in need of resuscitation, particularly in a contaminated environment may cause unintended further injury and create a potentially significant additional hazard to the non-breathing patient. This risk would be particularly acute in the case of an NBC (nuclear, biologic, chemical) hazard in the ambient environment.

The Flynn Bag Mask described in U.S. Pat. No. 4,532,923, is a respirator bag mask now popular with caregivers. The Flynn Bag Valve Mask is a football (egg) shaped, manually operable, shape deformably recoverable, bag formed from a ribbed, flexible thermoplastic including a valved air intake (rebreathing) at one end and a breathing/exhaust valve at the other end to which a mask to cover the nose and face is affixed or operably connected. The art also contains alternative manually operated resuscitation bag mask structures such as the self inflating bellows style bag disclosed in U.S. Pat. No. 4,870,962 to Sitnik. But none of these disclosed structures disclose or contemplate the use of a filter in conjunction with manually operable, resuscitation bag mask.

Filter cartridges and detachable filters are commonly used in combination with respirator/"gas" masks and other personal air supplies. Stern et al, U.S. Pat. No. 5,372,130, contains an exhaustive literature summary of filtered respirators and masks, some less complicated but others incorporating features, for example, of power supplies and fans. Such masks are typically employed in a "hot" /polluted environment where the elevated concentration of contaminants, smoke, toxic fumes, infectious agents, etc., present a hazard. The objective of filtered respiration equipment is to provide the user with filtered air and to minimize the risks associated with exposure to and contamination by a hazardous ambient atmosphere. An example of a common air filter used in both military and civilian applications for emergency protection in the presence of chemical, biological, and nuclear contamination, is the C2 filter cartridge. The C2 filter cartridge is typically employed for use in combination with respirator "gas" masks for short term, individual protection against airborne hazards.

In the field of resuscitation devices for use in emergency air management situations, the military currently employs a Resuscitation Device, Individual, Chemical. (RDIC) to provide filtered air to a patient during resuscitation procedures. However, the RDIC equipment suffers from being bulky, difficult to use and expensive.

What is needed in the art of emergency resuscitation devices is a simple, easily set up, effective, resuscitator unit.

SUMMARY OF THE INVENTION

It is an object of this invention to provide a resuscitation bag valve mask assembly with an air filter overcoming the problems with the prior art.

It is another object o this invention to provide a resuscitation bag/air intake filter combination that is at once effective, inexpensive and easily deployed in the field.

It is an object of the invention to provide delivery of clean air under positive pressure during airway management procedures.

It is a further object of this invention to provide an adapter for simple convertibility of conventional resuscitation bag bladders to accept and retain an air filter cartridge for filtering ambient air prior to introduction into a patient's airway.

A further object of this invention is to provide an assembly for adapting a C2 Filter cartridge to a bag valve mask.

Still a further object of this invention is to provide a method for attaching an air filter to a resuscitation bag mask for deployment and use in hazardous environments.

A further object of this invention is to provide an apparatus and method permitting conversion in a minimum of time of an ordinary, manually-operable, bag valve mask to a bag valve mask providing filtered, ambient air to a patient.

These and other objects of the invention are satisfied by a combination of a resiliently deformable, shape recoverable resuscitation bag with an air intake port and an air exhaust port, the bag incorporating a first member of the releasable bag interlocking member at the air intake port;

an adapter for removable attachment to the air intake port of a resuscitation bag, the adapter including a second element of a cooperating releasable bag interlocking member where the first and second releasable bag interlocking members cooperate to securely affix the adapter to the air intake port, the adapter also including a first element of a cooperating releasable filter retaining member; and a filter housing for holding an air filter and including a second cooperating element of the cooperating filter retaining member where the first and second elements cooperate to sealably secure the filter element to the adapter.

Still other objects of the invention are provided by a method for providing filtered air during resuscitation comprising the steps of selecting a shape recoverable, resiliently deformable resuscitation bag with an air intake port, securing a filter cartridge attachment adapter to the air intake port, securing a filter cartridge to the attachment adapter, and communicating air through the filter and air intake port and into the bag.

The invention herein is useful in rescue and lifesaving operations involving a wide range of situations involving, for example, chemical, smoke, and biological contamination. In keeping with the objectives, the invention is both simple and easily deployable in seconds. Based on its capabilities, the invention herein is readily operational in virtually any ambient environment and provides for clean filtered air under positive pressure delivered through a bag mask resuscitator. In part, owing to its ability to provide patient with a substantially containment free air supply, the invention reduces the hazard of additional injury to the patient from use of polluted/contaminated ambient air during emergency airway management procedures. Consequently, the invention is readily adapted for effective patient resuscitation requiring minimal cost and deployment time.

The foregoing and other objects and advantages will appear from the description to follow. In short, the invention herein, is directed particularly to a convertible, manually operable resuscitation bag valve mask providing maximum efficiencies using off-the-shelf basic components already being carried by military and civilian personnel and thereby requiring minimum additional storage space. In the description, reference is made to the accompanying drawing which forms a part hereof, and in which is shown by way of illustration a specific embodiment in which the invention may be practiced. This embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

FIG. 1 is an assembly view of a combination of a bag mask with a filter adapter and filter according to one embodiment of the invention.

FIG. 2 is side view of the filter adapter according to the embodiment of FIG. 1.

FIG. 3 is a cross-sectional longitudinal view of a filter adapter according to the embodiment of FIG. 1.

Figure 4:
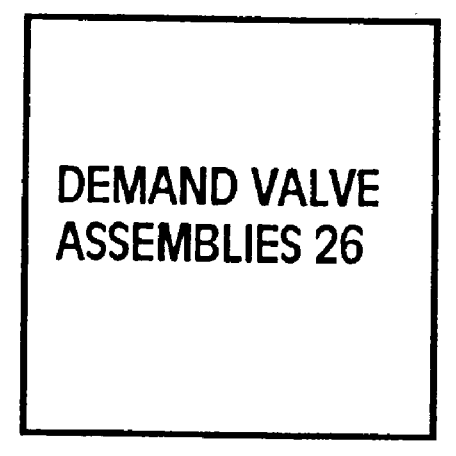

FIG. 4 shows a possible adjunct to an embodiment of the present invention.

DETAILED DESCRIPTION OF THE ILLUSTRATED EMBODIMENT

Referring now to the figures and, in particular, to FIG. 1 there is shown a bag valve mask resuscitator 10. The resuscitator 10 is characterized by a shape recoverable collapsible bladder 11 with an air intake port 12 disposed at one end (the rebreather side) incorporating a one-way valve 13 and, at the opposite end, a valved air exhaust port 14 (the breather side). By this arrangement, during expansion of the bladder, the negative pressure closes the valved air exhaust port 14 and draws air into the bladder through the intake port 12. On compression of the bladder, the one-way air intake valve 13 closes and the air contained in the bladder is forced under positive pressure, through exhaust port 14. Following release of the pressure on the bladder 11, the exhaust port valve closes and the air is drawn into the bladder via intake port 12 by negative pressure which opens the valve 13.

The mask assembly, designated M, for temporary sealing engagement to the patients face and, upon compression of the bladder 11, directing air to the patient's airway, may be of any conventional construction so long as it is sealingly attachable to the exhaust port 14 of the resuscitator 10. The bag mask resuscitator 10 is preferably of the type described in Flynn, U.S. Pat. No. 4,532,923, bag valve mask (BVM), the subject matter of which is incorporated by reference herein. The Flynn BVM resuscitator is available from O-Two Systems International, Inc. Such a bag mask is oblongated/football shaped, provides enhanced use gripping/manipulation, exhibits an excellent shape recovery/rebounding capacity following compression, is lightweight and portable, all desirable performance properties complementary to the objectives of the invention herein. The structure of the Flynn BVM has been recognized for Its utility and adaptability, particularly in the field, and can be outfitted with a variety of adjuncts such as nipples and/or demand valve assemblies 26 to provide Oxygen supplementation.

An adapter 15 is associated with the air intake port 12 and valve 13. Adapter 15 is composed of a rigid, strong material, e.g., metal or thermoplastic, preferably PVC, and provides a generally cylindrical shell 16 with an axially extending bore 17 defining an air channel. An exteriorly disposed annular groove 18 is dimensioned to receive and securely seat the rim of the intake port 12. Preferably, the bore 17 incorporates interior profiling, to facilitate construction and minimize accidental separation of the assembly during use which may occur from a simple interference fit. As illustrated, the profiling includes a selected length of internal screw threading 20 and an annular stop shoulder 21 at the terminus of the threading 20. The length of the screw threading must be sufficient to permit secure attachment of a filter cartridge 22 to the bag mask resuscitator assembly 10.

The filter cartridge 22 includes a filter housing 23 and a threaded neck connector 24. The diameter of the neck connector 24 corresponds to that of the bore 17 and the exterior screw threading corresponds to the threading 20 of the adapter 15. Furthermore, the threading 24 is of a pitch and length to allow the use to screw the neck 24 to progress axially until it positively abuts the stop shoulder 21 and establishes an airtight seal between the filter cartridge 22 and the adapter 15. While an interference fit, snap fit, or other equivalent construction can be used for the purpose of securing the filter cartridge 22 to the bag mask resuscitator 10, the illustrated threaded screw connection between the filter cartridge and the adapter 15 is the preferred connection means as it provides the user with a high degree of confidence in the assembly integrity of the invention, particularly, in field use.

The invention contemplates retrofitting existing BVM assemblies with a filtered cartridge adapter. Consistent with the foregoing, it is necessary for the adapter 15 to be dimensioned to complement the air intake port 13 of the bladder 11. The particulars of the filter cartridge connection may be altered in order to adapt to other off-the-shelf filter cartridge housings and off-the-shelf resuscitation bladders. In such a case, the outer diameter of the adapter 15 would be slightly larger than the rim of the bladder the inherent elasticity of which will provide adequate hoop strength to seat in the groove 18. Thus, once assembled, there is an airtight seal between the adapter and bladder of sufficient strength to prevent unintended separation of these two assembly components during use.

Given the foregoing structures, the use of the invention is now described in connection with the use of a C2 Filter. Once the adapter 15 has been affixed to the bladder 11, the ability to reconstruct a BVM resuscitator from standard use to a chemical and biological application can be accomplished in less then 10 seconds. First, the non-threaded side of the adapter 15 is twisted into the rebreather/air intake 12 the resuscitator bladder 11. Next, screw the C2 filter canister housing 22 clockwise until its axial progress is stopped by stop shoulder 21 end of the adapter. Finally, at the breathing/air exhaust end of the bladder affix the appropriate mask assembly M. The assembly is now ready for use in resuscitation procedures and airway management in a polluted/toxic ambient environment.

In tests, a construct according to the invention proved to be practicable. The test was performed using a mask placed over a mannequin headform and exposed to a vapor generator providing an atmosphere of methyl salicylate at a concentration of 10 mg/m$^3$ for 40 minutes. The mannequin face included air sampling lines connected to a Minicams® gas monitoring system (CMS Field Products Group, Birmingham, Ala.) and a sorbant tube sampler connecting a plurality of sorbant containing tubes via a series of electronically timed solenoid valves, and a flowmeter, to a vacuum pump. The sorbant tubes, are filled with TENEX. Each tube was sampled for 10 minutes at a 1 L/min flow rate. The tubes were then analyzed in a Perkin Elmer Sigma 2000 GC using a flame ionization detector. The data obtained from the test demonstrated that the mask constructed according to the invention successfully removed in excess of 99% in each instance.

It should be appreciated that the invention is not limited to use with a specific resuscitation mask but can be adapted to other available systems such as those available from Ambu, Inc., Hamilton Medical, Inc., Laerdal Medical Corp., etc. Furthermore, the skilled artisan should readily appreciate that the invention can be employed with standard airway equipment currently in use such as endotracheal tubes, esophageal obdurator airways, and esophageal gastric tubes.

Given the foregoing, it should be apparent that the specific described embodiments are illustrative and not intended to be limiting. Furthermore, variations and modifications to the invention should now be apparent to a person having ordinary skill in the art. These variations and modifications are intended to fall within the scope and spirit of the invention as defined by the following claims.

I claim:

1. In combination:
    a resiliently deformable, shape recoverable resuscitation bag with an air intake port and an air exhaust port, said bag incorporating a first releasable bag interlocking member at the air intake port;
    an adapter for removable attachment to said air intake port of a resuscitation bag, the adapter including a second releasable bag interlocking member where said first and second releasable bag interlocking members cooperate to securely affix the adapter to the air intake port, said adapter also including a first element of a cooperating releasable filter retaining member; and
    a filter housing for holding an air filter and including a second element of said cooperating releasable filter retaining member where said first and second elements cooperate to sealably secure said filter housing to said adapter.

2. The combination of claim 1 where the bag defines an oblong shape.

3. The combination according to claim 1 where the bag is oblongated with first and second ends respectively containing said air intake and air exhaust ports where said ports feature one way air flow valves allowing air to move in only one direction upon compression and recovery of the bag.

4. The combination according to claim 3 further comprising a mask for placing over a patients face.

5. The combination according to claim 4 further comprising a means for supplementing the air with oxygen.

6. The combination according to claim 3 where the second interlocking member comprises an annular ring disposed about the outer circumference of the adapter and the first interlocking member is defined by the air intake port which is sized to annularly clamp into the annular ring.

7. The combination according to claim 6 where the filter retaining members comprise screw threading and the filter is attached to the adapter by screwing the filter housing into the adapter.

8. A manually operated resuscitator comprising:
    a bag valve bladder including a rebreathing air intake port for drawing air into the bladder, said air intake port including valve means for limiting the direction of airflow out of the bladder via the air intake port, and an air exhaust port for exhausting air under manual pressure applied to the bladder; and
    an adapter for releasably affixing an air filter cartridge to said air intake port to filter air flowing into the bag from the air intake port.

9. A method for providing filtered air during resuscitation comprising the steps of:
    selecting a shape recoverable, resiliently deformable resuscitation bag with an air intake port, and a valve that limits airflow out of the bag via the air intake port;
    securing a filter cartridge attachment adapter to the air intake port;
    securing a filter cartridge to the attachment adapter;
    manually actuating the recsusitation bag to provide;
    communicating air through the filter cartridge and air intake port and into the bag; and
    manually compressing the bag to force air, under pressure to a face mask through an exhaust port.

* * * * *